(12) United States Patent
Aron et al.

(10) Patent No.: US 7,650,193 B2
(45) Date of Patent: Jan. 19, 2010

(54) LEAD ASSEMBLY WITH POROUS POLYETHYLENE COVER

(75) Inventors: Rebecca Aron, Ann Arbor, MI (US); Mohan Krishnan, Shoreview, MN (US); Kevin Ely, Blaine, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 614 days.

(21) Appl. No.: 11/150,549

(22) Filed: Jun. 10, 2005

(65) Prior Publication Data

US 2006/0282146 A1    Dec. 14, 2006

(51) Int. Cl.
*A61N 1/04* (2006.01)
*A61B 5/04* (2006.01)

(52) U.S. Cl. ............... 607/122; 607/121; 600/372; 600/373; 600/374

(58) Field of Classification Search .......... 607/115, 607/121, 122; 600/372–374
See application file for complete search history.

(56) References Cited

U.S. PATENT DOCUMENTS

| | | | |
|---|---|---|---|
| 4,149,542 A | 4/1979 | Thoren | |
| 4,344,908 A | 8/1982 | Smith et al. | |
| 4,356,138 A | 10/1982 | Kavesh et al. | |
| 4,413,110 A | 11/1983 | Kavesh et al. | |
| 4,430,383 A | 2/1984 | Smith et al. | |
| 4,536,536 A | 8/1985 | Kavesh et al. | |
| 4,551,296 A | 11/1985 | Kavesh et al. | |
| 5,090,422 A | 2/1992 | Dahl et al. | |
| 5,324,324 A | 6/1994 | Vachon et al. | |
| 5,620,451 A | 4/1997 | Rosborough | |
| 5,755,762 A | 5/1998 | Bush | |
| 5,931,862 A | 8/1999 | Carson | |
| 6,701,191 B2 | 3/2004 | Schell | |
| 2003/0023294 A1 | 1/2003 | Krall et al. | |
| 2003/0124279 A1 | 7/2003 | Sridharan et al. | |
| 2004/0059402 A1* | 3/2004 | Soukup et al. | 607/116 |
| 2005/0060004 A1 | 3/2005 | Cooke et al. | |

FOREIGN PATENT DOCUMENTS

| | | |
|---|---|---|
| GB | 2240721 | 8/1991 |
| WO | WO-02089909 A1 | 11/2002 |
| WO | WO-03047688 A1 | 6/2003 |
| WO | WO-2006/135754 A1 | 12/2006 |

OTHER PUBLICATIONS

"International Search Report and Written Opinion for Application No. PCT/US2006/022496, Date mailed Nov. 3, 2006", 12 Pages.

Knapp, Christopher P., et al., "Polymer Lead Covering With Varied Material Properties", U.S. Appl. No. 11/150,021, filed Jun. 10, 2005, 26 Pages.

"European Application Serial No. 06772702.4, Office Action mailed May 6, 2008", 6 pages.

* cited by examiner

*Primary Examiner*—Carl H. Layno
*Assistant Examiner*—Tammie K Heller
(74) *Attorney, Agent, or Firm*—Schwegman, Lundberg & Woessner, P.A.

(57) ABSTRACT

This document discusses, among other things, a lead assembly including a porous polyethylene cover. In an example, the cover includes sections that have differing pore sizes. In an example, a section of the cover near a distal end portion of a lead assembly includes pores that are large enough to allow tissue ingrowth. In another example, a lead assembly includes two or more polyethylene covers having different porosities.

15 Claims, 6 Drawing Sheets

LEAD ASSEMBLY WITH POROUS POLYETHYLENE COVER

TECHNICAL FIELD

This patent document pertains generally to medical device lead assemblies, and more particularly, but not by way of limitation, to porous polyethylene covers for a medical device lead assembly.

BACKGROUND

Medical devices such as pacers and defibrillators typically include at least one lead assembly. In a defibrillator, for example, a lead assembly typically includes at least one defibrillation electrode, such as a defibrillation coil. Some lead assemblies include a cover that extends over at least a portion of the outer surface of the lead assembly. A cover may extend over a defibrillation coil, for example. Covers are used, for example, to prevent tissue ingrowth.

United States Published Patent Application No. 2003/0023294A1 describes an expanded polytetrafluorethylene (ePTFE) cover. Expanded polytetrafluoroethylene has a high melting point (over 300 degrees C.) and a high melt viscosity. The application of an ePTFE cover to a defibrillation electrode can involve sintering at high temperatures. Improved coverings for lead assemblies are needed.

SUMMARY

An example lead assembly includes a lead body, a conductor extending through the lead body, an electrode coupled to the conductor, and a cover formed from porous polyethylene extending over the electrode. In an example, the cover includes a first section having tissue ingrowth allowing pores and a second section having tissue ingrowth inhibiting pores. In an example, the cover is formed from at least one piece of polyethylene wrapped around at least a portion of the electrode, the first section of the cover wrapped with a first tension, and the second section wrapped with a second tension that is different from the first tension. In an example, the piece of porous polyethylene is laser-sintered to itself. In an example, the cover extends over substantially all of the lead body.

In another example, a lead assembly includes a lead body, a conductor extending through the lead body, an electrode coupled to the conductor, and a piece of mechanically stretched ultra high molecular weight polyethylene wrapped around at least a portion of the electrode. In an example, the piece of ultra high molecular weight polyethylene has a consistent pore size. In an example, the piece of mechanically stretched ultra high molecular weight polyethylene is hydrophilic.

An example method includes wrapping a first piece of porous polyethylene material around a first portion of a lead assembly, and fusing a first portion of the first piece of porous polyethylene material to a second portion of the first piece of porous polyethylene material. In an example, the wrapping includes wrapping the piece of porous polyethylene material under tension and controlling the size of the pores in the polyethylene. In an example, controlling the size of the pores in the polyethylene includes adjusting the tension. In an example, the method further includes wrapping a second piece of porous polyethylene material around a second portion of the lead assembly, the second portion having pores that are larger than pores in the first piece of porous polyethylene material. In an example, the method further includes joining the second piece of porous polyethylene to the first piece of porous polyethylene. In an example, fusing the piece of porous polyethylene includes heating the piece of porous polyethylene to between 80 and 150 degrees. In an example, the method further includes hydrophilicly treating at least a portion of the first piece of porous polyethylene.

BRIEF DESCRIPTION OF THE DRAWINGS

In the drawings, which are not necessarily drawn to scale, like numerals describe substantially similar components throughout the several views. The drawings illustrate generally, by way of example, but not by way of limitation, various embodiments discussed in the present document.

DETAILED DESCRIPTION

The following detailed description includes references to the accompanying drawings, which form a part of the detailed description. The drawings show, by way of illustration, specific embodiments in which the invention may be practiced. These embodiments are also referred to herein as "examples." The drawings and following detailed description is not to be taken in a limiting sense, and the scope of the present invention is defined by the appended claims and their equivalents.

Figure 1:
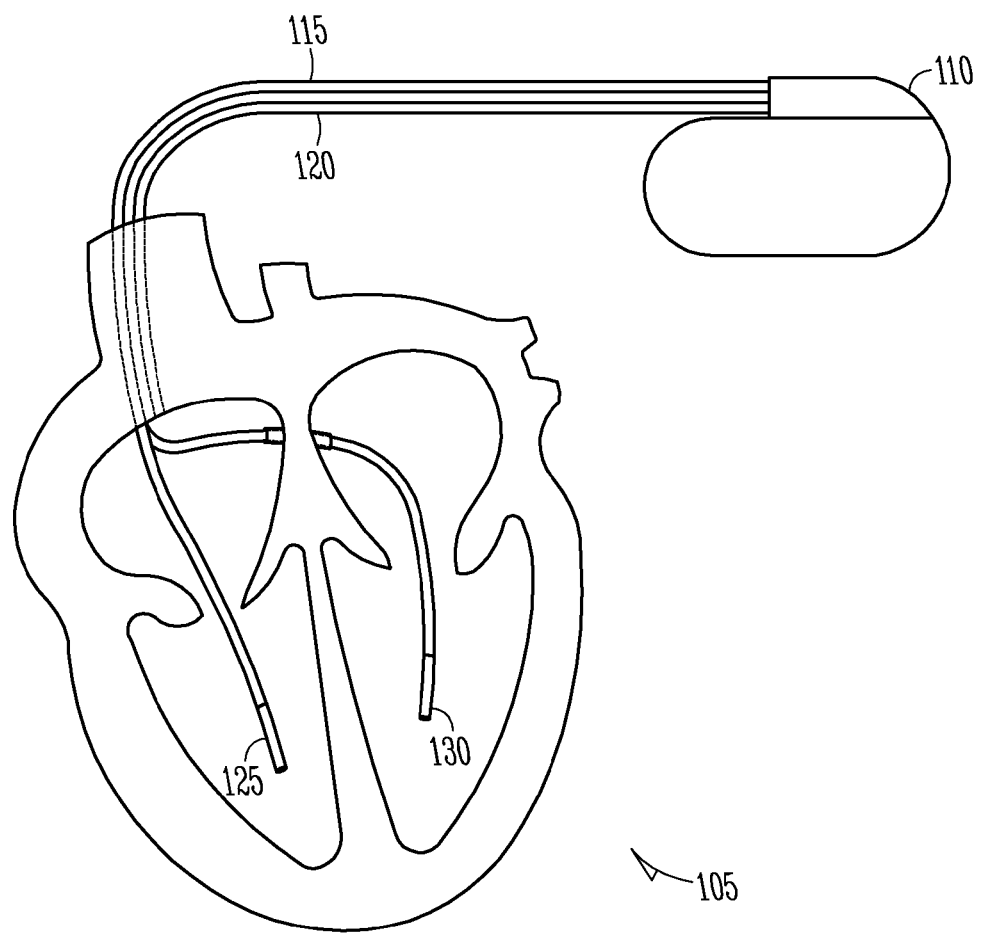
FIG. 1 shows an example system for monitoring and stimulating a heart.

A lead assembly includes a porous polyethylene cover extending over at least a portion of the length of the lead assembly. FIG. 1 shows an example system for monitoring and stimulating a heart that includes a lead assembly having a porous polyethylene cover. FIGS. 2, 3A-3B, 4, 5, and 6A-6B show lead assemblies and example porous polyethylene covers. FIG. 7 is a flowchart that illustrates a method of applying a cover.

Referring now to FIG. 1, an example system for monitoring and stimulating a heart 105 includes a medical device 110 and at least one lead assembly. In an example, the lead assembly is a pacing lead, defibrillation lead, or neurological lead. In an example, the medical device 110 is a pacer, defibrillator, or stimulator. In an example, the medical device 110 is coupled to two lead assemblies, as shown in FIG. 1. In FIG. 1, one lead assembly 115 extends into the right side of the heart. The other lead assembly 120 extends into the left side of the heart. Each lead assembly includes at least one porous polyethylene cover 125, 130. In another example, the medical device 110 is coupled to a single lead assembly that extends, for example, into either the right or left side of the heart. In other examples, a lead assembly extends on or around the heart, or on or around a nerve truck or other anatomical target.

Figure 2A:
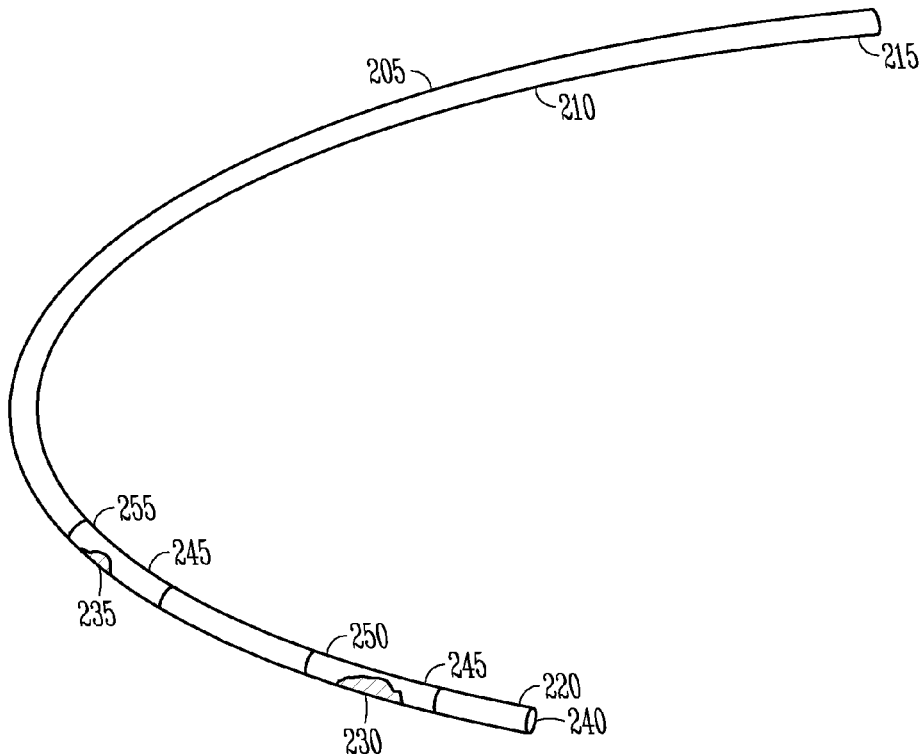
FIG. 2A shows a medical device lead assembly that includes a cover over an electrode.
Figure 2B:
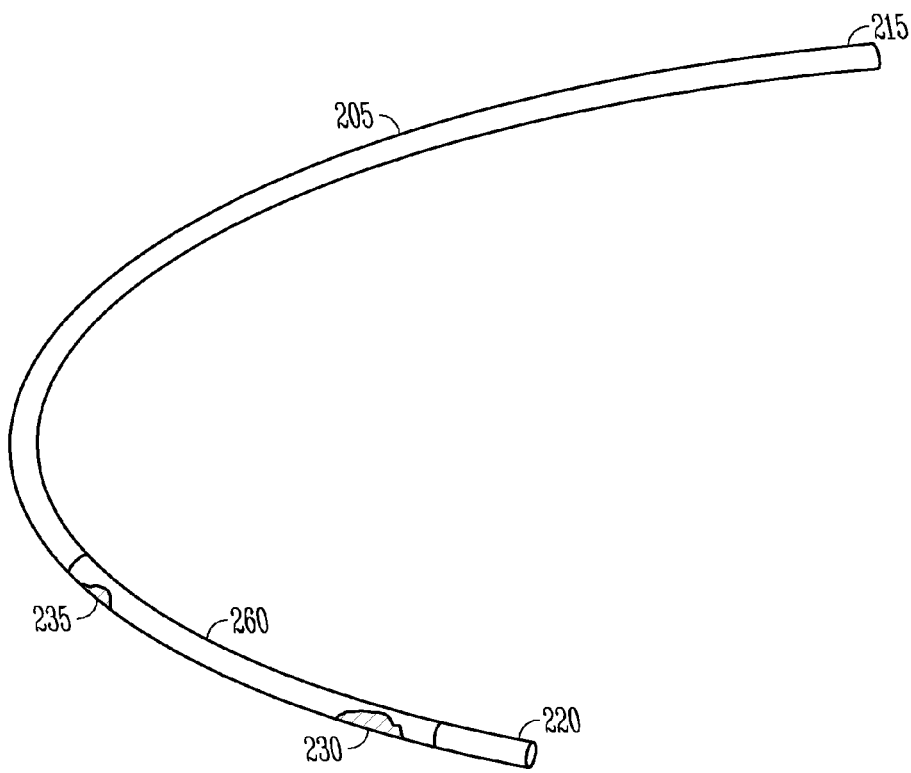
FIG. 2B shows a medical device lead assembly that includes a cover over two electrodes.

FIG. 2A shows an example medical device lead assembly 205. The lead assembly 205 includes one or more conductors extending through a lumen in a lead body 210. In an example, the lead body 210 is made of silicone. In an example, the lead body is a silicone tube. A proximal end 215 of the lead assembly 205 is connectable to a medical device. A distal end portion 220 of the lead assembly is implantable in, on, or around a heart. The conductors in the lead assembly are electrically coupled to one or more electrodes. In an example, the lead assembly includes a first defibrillation electrode 230, a second defibrillation electrode 235, and a sensing/pacing electrode 240. A porous polyethylene covering 245 extends over at least one of the defibrillation electrodes. In an example, a first covering 250 extends over the first defibrillation electrode 230 and a second covering 255 extends over the second defibrillation electrode 235. The coverings are shown partially cut-away in FIG. 2A to show the electrodes beneath the coverings. In an example, the coverings are spaced apart on the lead assembly. In another example, the coverings touch or overlap, and are optionally joined together. In an alternative example, a single covering 260 extends over both the first defibrillation electrode 230 and the second defibrillation electrode 235, as shown in FIG. 2B.

In an example, the thickness of the polyethylene covering is between 0.0001 and 0.010 inches, the width of the covering is between 0.1 and 8 inches, and the pore size is between 0.1 micron and 15 microns. In an example, the polyethylene covering shown in FIG. 2A or 2B has a tensile strength of about 1000 pounds per square inch (psi) and pore size of about 2 microns.

In an example, a porous polyethylene covering is applied to an electrode in line with other manufacturing processes. Examples polyethylene materials have a processing temperature of around 130-150° C., which allows application of the polyethylene covering in a manufacturing line. In contrast, materials such as PTFE can have processing temperatures in excess of 300° C. To accommodate the high-temperature sintering, a PTFE covering is typically added to a lead assembly in a post process. Forming a cover from polyethylene allows the cover to be applied in-line with other manufacturing steps because of the 130-150° C. processing temperatures associated with polyethylene. For example, polyethylene can be applied by spray coating, dip coating, plasma deposition, laser deposition, or chemical vapor deposition.

Figure 3A:
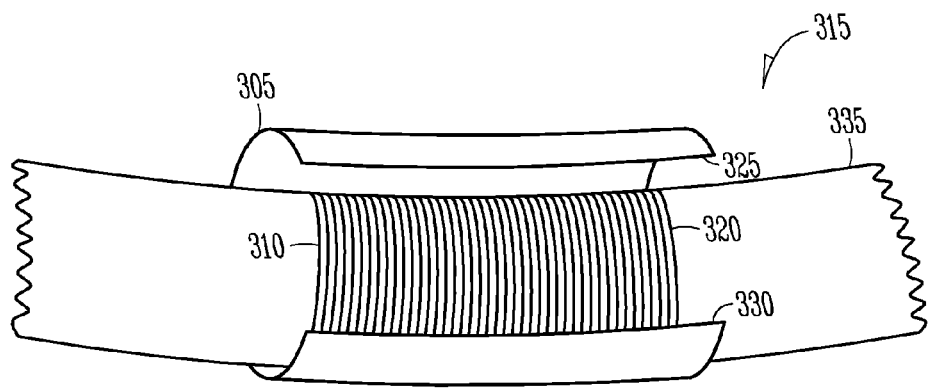
FIGS. 3A and 3B show a polyethylene cover wrapped around a portion of a medical device lead assembly.
Figure 3B:
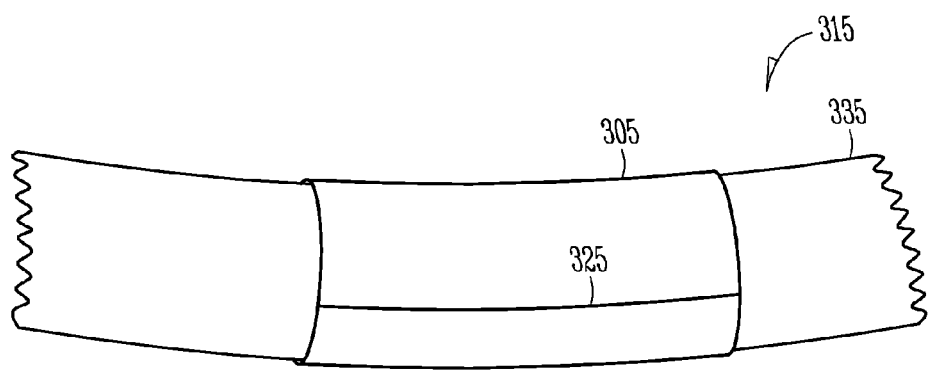

Referring now to FIGS. 3A and 3B, an example method of forming a polyethylene covering on a lead assembly is shown. A piece of porous polyethylene material 305 is wrapped around at least a portion of a lead assembly 315. The piece includes a first edge 325 and a second edge 330. The first edge 325 meets or overlaps with the second edge 330, as shown in FIG. 3B. In an example, the piece of porous polyethylene material 305 is wrapped around an electrode 310. In an example, the electrode 310 includes a wire 320 wrapped into a coil, and the polyethylene material covers the entire coil. In an example, the piece of porous polyethylene also extends over at least a portion of a lead body 335. In an example, the cover extends over most or all of the lead assembly.

The polyethylene cover 305 is secured on the lead assembly, for example, by connecting the cover to itself. In an example, at least a portion of the polyethylene cover 305 is heated to fuse the porous polyethylene material to itself. In an example, the heating also conforms the polyethylene to the outer shape of the electrode or lead body. In an example, the polyethylene material 305 is sintered proximate the first edge 325 to hold the material 305 in a generally tubular shape that extends over the electrode, as shown in FIG. 3B. In an example, the porous polyethylene covering is sintered with a laser, infrared (IR) wand, heat gun, or oven.

Figure 4:
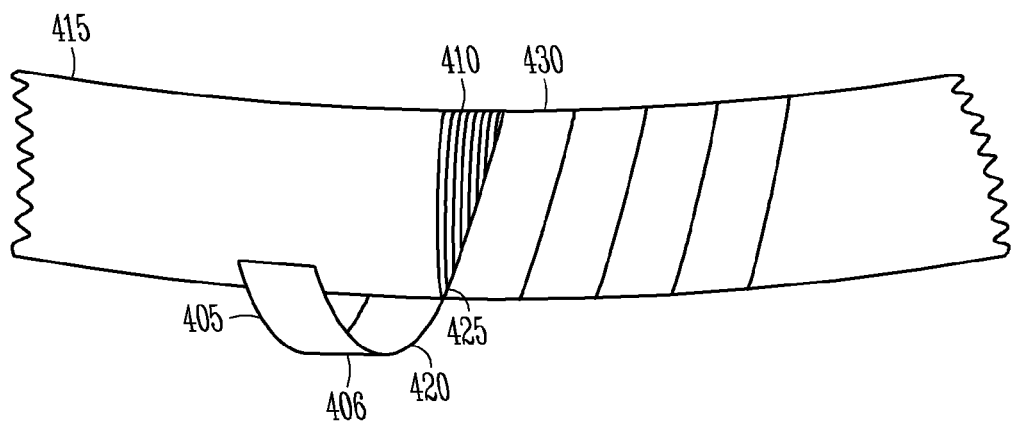
FIG. 4 shows a piece of polyethylene material wrapped around a portion of a medical device lead assembly to form a cover.

Referring now to FIG. 4, another method of applying a polyethylene covering is shown. A piece 405 of polyethylene material 406 is wrapped around a lead assembly 415 in a spiral. In an example, the piece 405 is wrapped around an electrode 410. In an example, a first edge 420 of the piece 405 meets or overlaps with a second edge 425 of the piece from a previous wrap around the lead assembly. The spiral-wrapped piece of polyethylene forms a polyethylene tube 430 that extends over the electrode.

In an example, spiral-wrapped polyethylene material as shown in FIG. 4 extends past the electrode to cover a portion of the lead assembly, or all of the lead assembly. Covering the lead assembly protects the lead assembly and facilitates extraction, for example by limiting or preventing tissue ingrowth around portions of the lead.

Figure 5:
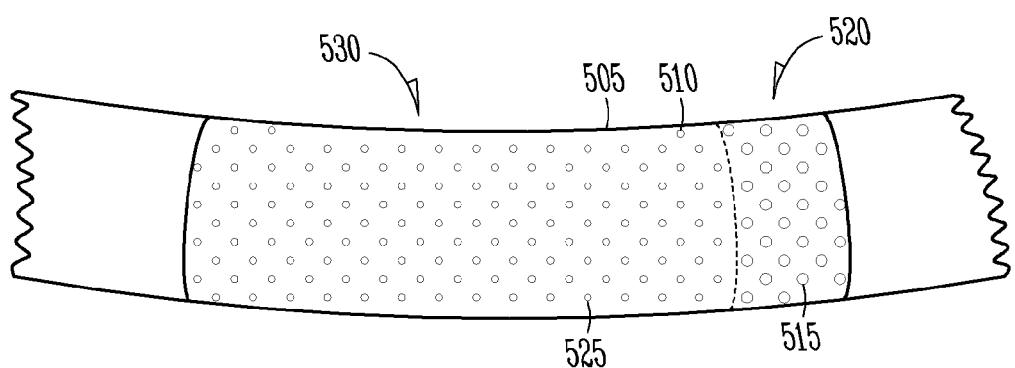
FIG. 5 shows a porous cover having pores of different sizes in different regions of the cover.

Referring now to FIG. 5, a polyethylene covering 505 includes pores 510. The size of the pores is exaggerated for the purpose of illustration. In an example, the pore size in the porous polyethylene covering is controlled to control tissue ingrowth into the covering. In an example, the pores 515 in a first portion 520 of the polyethylene covering 505 are smaller than the pores 525 in a second portion 530 of the polyethylene covering. For the purpose of illustration, a dotted line is provided FIG. 5 to distinguish the first portion 520 of the covering from the second portion 530. In an example, the pores 515 in the first portion 520 are large enough to allow at least some tissue ingrowth, and the pores 525 in the second portion 530 are small enough to substantially inhibit tissue ingrowth. In an example, the tissue ingrowth into the pores 515 in the first portion 520 secures the lead to body tissue. In an example, the covering 505 is formed around the lead assembly using the technique illustrated in FIGS. 3A-3B or the technique illustrated in FIG. 4.

The size of pores in the polyethylene material can be controlled using one or more of a variety of techniques. In an example, pieces of polyethylene material are manufactured to have differing pore sizes by controlling parameters such as tension or heat during the manufacturing process. In an example, different polyethylene pieces are used at different locations on the lead assembly to allow tissue growth at particular locations on the lead, such as at a distal end portion.

In another example, pore size is controlled by adjusting tension applied to the polyethylene material as the material is assembled onto the lead assembly. In an example, a polyethylene cover is made using a spiral winding technique, as illustrated in FIG. 4, and the pore size is controlled by varying the tension on the piece of material 305. In another example, pore size is varied through application of heat during or after the application of the polyethylene material to the electrode. In an example, two or more of the preceding techniques are used concurrently or sequentially to control the pore size at one or more locations in the polyethylene material. In an example, laser drilling is used to form pores in a specific size and pattern.

Figure 6A:
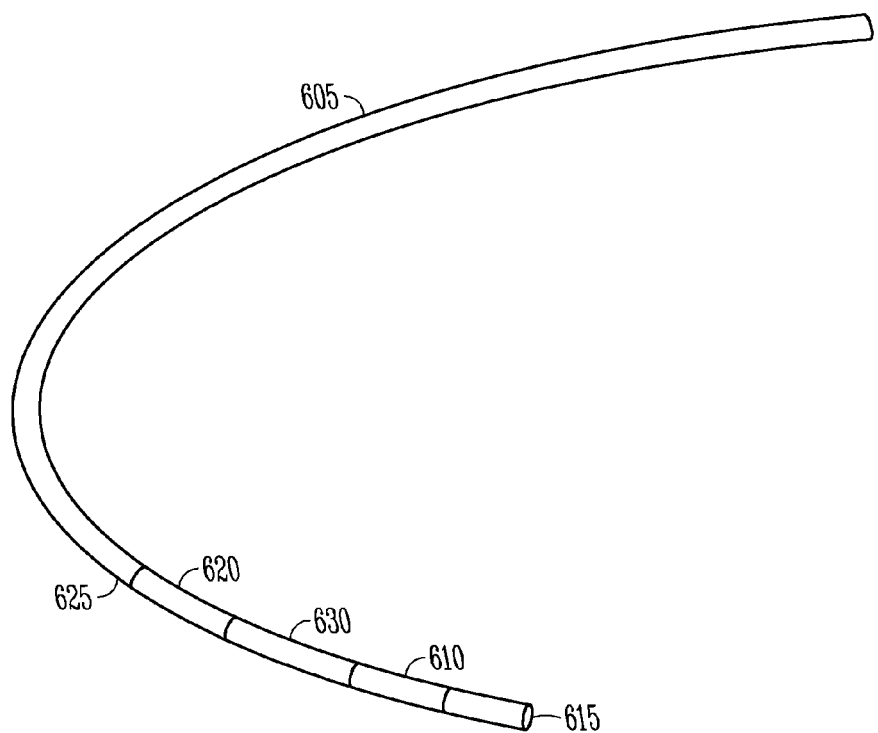
FIG. 6A shows a lead assembly and porous covers that have pores of different sizes.
Figure 6B:
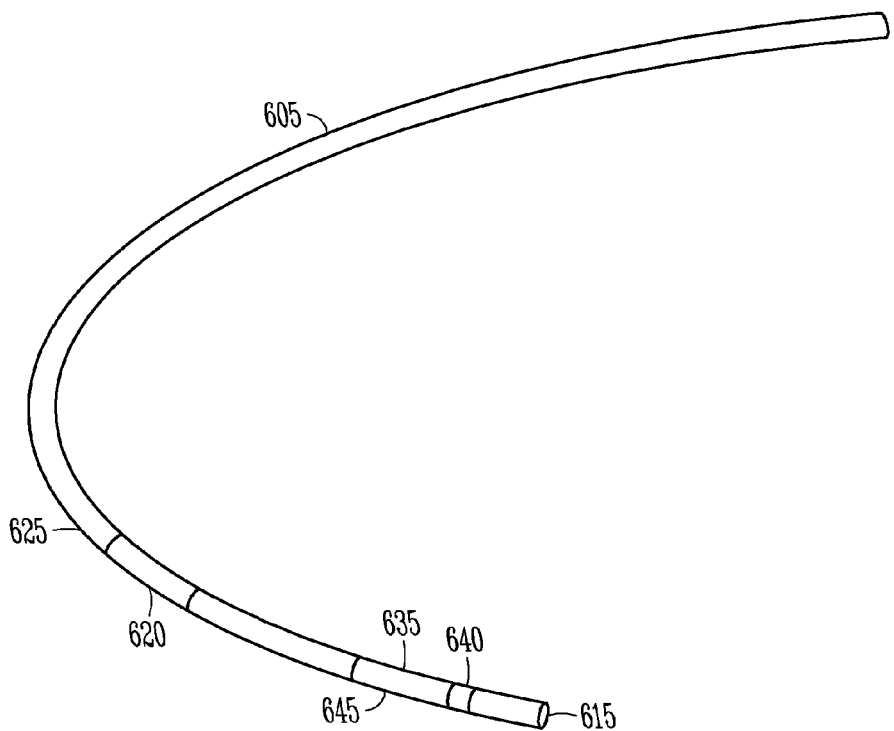
FIG. 6B shows a lead assembly and a porous cover that has pores in a distal portion of the cover that are larger than pores elsewhere in the cover.
Figure 7:
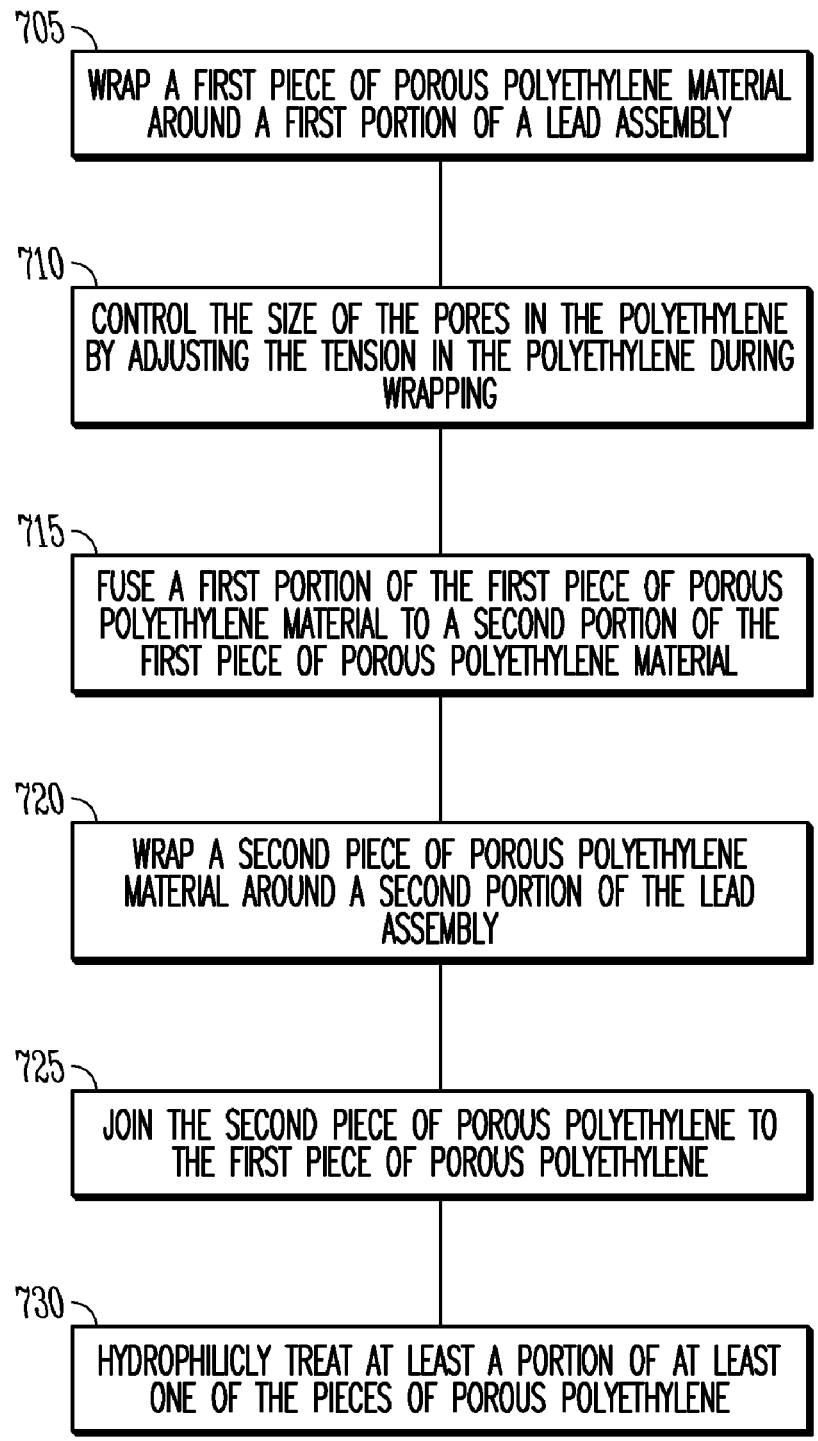
FIG. 7 is a flow chart that illustrates a method of applying polyethylene material to a lead assembly.

Referring now to FIG. 6A, a lead assembly 605 includes a first porous polyethylene cover 610 proximate a distal end portion 615 of the lead assembly and a second polyethylene cover 620 proximate a middle portion 625 of the lead assembly. In an example, the lead assembly includes a third cover 630 that extends between the first cover 610 and second cover 620. Other examples include additional polyethylene covers. In an example, covers extend over most or all of the outer surface of the lead assembly. In an example, some or all of the polyethylene covers are fused together using heat. In an example, the ends of adjacent covers are fused together using a laser.

In an example, a portion of the polyethylene cover 610 proximate the distal end portion of the lead assembly 605 includes pores that are large enough to permit tissue growth. The tissue growth secures the distal end portion of the lead to local tissue. For example, when the lead is implanted in the heart, the tissue growth secures the distal end portion of the lead to the heart.

In an example, pore size is controlled within one or both of the covers 610, 620, which allows for selective tissue ingrowth at locations on the cover. In the example shown in FIG. 6B, a cover 635 includes a first portion 640 that includes pores that are large enough to allow tissue ingrowth, and a second portion 645 that has pores that do not allow tissue ingrowth. In an example, the first portion 640 is formed having larger pores than the second portion 645 by varying parameters such as tension and/or heat during application of the polyethylene to the lead assembly. In another example, the first portion 640 is made from a separate piece of polyethylene material that has been pre-processed to have larger pores than the second portion 645. In an example, the separate piece is applied to the lead in a separate operation and then sintered to the second portion to form a continuous cover In an example, the covering is hydrophilicly treated. In an example, the covering is wetted using a plasma technique. In another example, the covering is wetted using a plasma-assisted chemical vapor deposition technique. In an example, the covering is treated using, glycol, acrylic acid, allyl amine, an alcohol such as isopropyl alcohol (IPA), ethanol, or methanol. In an example, the covering is treated with a laser after the covering is wetted to preserve the hydrophilic state of the covering. In an example, the wavelength, pulse duration, and/or power are adjusted to actuate the polymer surface and promote development of a hydrophilic state. In another example, a chemical hydrophilic treatment is used. In an example, the chemical hydrophilic treatment uses polyvinyl acetate (PVA) or polyethylene glycol (PEG).

In an example, when the pores are filled with a conductive substance, such as body fluid, the pores in the polyethylene provide a conductive pathway for a defibrillation current. In another example, the polyethylene includes particles of conductive matter to make the covering itself conductive. In another example, a conductive material is deposited on the polyethylene to provide a conductive pathway for a defibrillation current.

FIG. 7 is a flow chart that illustrates a method of applying a polyethylene material to a lead assembly. At 705, a piece of porous polyethylene material is wrapped around a first portion of a lead assembly. In an example, the stock polyethylene material is porous before it is wrapped. In another example, pores are created in the polyethylene when the polyethylene is wrapped. At 710, the size of the pores in the polyethylene is controlled by adjusting a tension in the polyethylene during wrapping. Applying a higher tension to the polyethylene results in more stretching of the material and larger pores. At 715, a first portion of the piece of porous polyethylene is fused to a second portion of the piece of polyethylene. In an example, the polyethylene is wrapped spirally onto the lead assembly, and adjacent portions of the material (i.e. adjacent windings) are fused together. In an example, the polyethylene is fused by heating, for example with a laser. In an example, the porous polyethylene is heated to between 80 and 150 degrees C.

Referring again to FIG. 7, at 720, a second piece of porous polyethylene is wrapped around a second portion of the lead assembly. In an example, the second piece of polyethylene has pores that are larger than the pores in the first piece of porous polyethylene. In an example, the second piece of porous polyethylene is wrapped onto the lead assembly before the first piece of porous polyethylene is wrapped onto the lead assembly. At 725, the second piece of porous polyethylene is joined to the first piece of porous polyethylene. In an example the second piece of porous polyethylene is fused to the first piece of porous polyethylene by heating the polyethylene, for example with a laser.

At 730, at least a portion of at least one piece of porous polyethylene is hydrophilically treated. In an example, a hydrophilic agent is deposited on one or both of the pieces of porous polyethylene. In an example, a hydrophilic agent is deposited in a plasma-assisted chemical vapor deposition process. In an example, hydrophilicly treating at least a portion of the piece of porous polyethylene includes treating the first piece of polyethylene with a laser. In an example, laser treating the porous polyethylene preserves hydrophilicity imparted by a hydrophilic agent. In an example, hydrophilicly treating at least a portion of the piece of porous polyethylene includes chemically treating the first piece of polyethylene. In an example, the chemical treatment preserves hydrophilicity imparted by a hydrophilic agent. In an example, the chemical hydrophilic treatment uses polyvinyl acetate (PVA) or polyethylene glycol (PEG).

Polymer lead coverings having varied material properties are also described in application Ser. No. 11/150,021, filed Jun. 10, 2005, now issued as U.S. Pat. No. 7,366,573 to Knapp et al., entitled Polymer Lead Covering with Varied Material Properties, which is incorporated by reference in its entirety.

It is to be understood that the above description is intended to be illustrative, and not restrictive. Since many embodiments of the invention can be made without departing from the scope of the invention, the invention resides in the claims hereinafter appended.

What is claimed is:

1. A lead assembly comprising:
   a lead body;
   a conductor extending through the lead body;
   an electrode coupled to the conductor;
   a porous polyethylene cover extending over the electrode; and
   wherein the cover includes a first section having tissue ingrowth allowing pores and a second section having tissue ingrowth inhibiting pores, and the first section is at a different longitudinal location than the second section.

2. The lead assembly of claim 1, wherein the cover is formed from at least one piece of polyethylene wrapped around at least a portion of the electrode, the first section of the cover wrapped with a first tension, and the second section wrapped with a second tension that is different from the first tension.

3. The lead assembly of claim 2, wherein the piece of porous polyethylene is laser-sintered to itself.

4. The lead assembly of claim 3, wherein the piece of porous polyethylene is spirally wrapped around the electrode.

5. The lead assembly of claim 1, where the first section is formed from a first piece of porous polyethylene and the second section is formed from a second piece of porous polyethylene, the first piece of porous polyethylene having larger pores than the second piece of porous polyethylene.

6. The lead assembly of claim 5, wherein the first piece of porous polyethylene is joined to the second piece of porous polyethylene.

7. The lead assembly of claim 1, wherein the second section of the cover is proximate a distal end portion of the lead assembly.

8. The lead assembly of claim 1, wherein the cover extends over substantially all of the lead body.

9. The lead assembly of claim 1, wherein the porous polyethylene cover is a piece of mechanically stretched ultra high molecular weight polyethylene wrapped around at least a portion of the electrode.

10. The lead assembly of claim 9, wherein the piece of mechanically stretched ultra high molecular weight polyethylene is wrapped around at least a portion of the lead body.

11. The lead assembly of claim 9, wherein the piece of mechanically stretched ultra high molecular weight polyethylene is hydrophilic.

12. A lead assembly comprising:
a lead body;
a conductor extending through the lead body;
an electrode coupled to the conductor;
a porous polyethylene cover extending over the electrode, the cover includes a first section having tissue ingrowth allowing pores and a second section having tissue ingrowth inhibiting pores;
the first section having larger pores than the second section of porous polyethylene, and the first section is joined with the second section and is a continuous cover over the electrode, and the first section is at a different longitudinal location than the second section.

13. The lead assembly as recited in claim 12, wherein the pores are filled with conductive substance.

14. The lead assembly as recited in claim 12, wherein the first section is fused with the second section.

15. The lead assembly as recited in claim 12, wherein the porous polyethylene cover further includes a hydrophilically treated portion.

* * * * *

UNITED STATES PATENT AND TRADEMARK OFFICE
CERTIFICATE OF CORRECTION

PATENT NO. : 7,650,193 B2 Page 1 of 1
APPLICATION NO. : 11/150549
DATED : January 19, 2010
INVENTOR(S) : Aron et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1131 days.

Signed and Sealed this

Twenty-eighth Day of December, 2010

David J. Kappos
*Director of the United States Patent and Trademark Office*